(12) United States Patent
Jegou

(10) Patent No.: US 12,083,213 B2
(45) Date of Patent: *Sep. 10, 2024

(54) PROCESS FOR DYEING HAIR COMPRISING AT LEAST ONE PIGMENT, AT LEAST ONE ACRYLATE-FUNCTIONALIZED POLYMER AND AT LEAST ONE FUNCTIONALIZED SILICONE CHOSEN FROM SILICONES FUNCTIONALIZED WITH AT LEAST ONE MERCAPTO OR THIOL GROUP

(71) Applicant: L'OREAL, Paris (FR)

(72) Inventor: Gwenaelle Jegou, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 256 days.

This patent is subject to a terminal disclaimer.

(21) Appl. No.: 16/500,688

(22) PCT Filed: Apr. 9, 2018

(86) PCT No.: PCT/EP2018/059038
§ 371 (c)(1),
(2) Date: Oct. 3, 2019

(87) PCT Pub. No.: WO2018/185339
PCT Pub. Date: Oct. 11, 2018

(65) Prior Publication Data
US 2020/0368140 A1 Nov. 26, 2020

(30) Foreign Application Priority Data

Apr. 7, 2017 (FR) ........................ 1753079

(51) Int. Cl.
*A61K 8/895* (2006.01)
*A61K 8/898* (2006.01)
*A61K 8/899* (2006.01)
*A61Q 5/06* (2006.01)

(52) U.S. Cl.
CPC .............. *A61K 8/895* (2013.01); *A61K 8/898* (2013.01); *A61K 8/899* (2013.01); *A61Q 5/065* (2013.01); *A61K 2800/43* (2013.01); *A61K 2800/594* (2013.01); *A61K 2800/882* (2013.01)

(58) Field of Classification Search
None
See application file for complete search history.

(56) References Cited

U.S. PATENT DOCUMENTS

| | | | |
|---|---|---|---|
| 5,166,276 A | 11/1992 | Hayama et al. | |
| 5,708,070 A | 1/1998 | Joffre et al. | |
| 5,807,543 A | 9/1998 | Coffindaffer et al. | |
| 6,451,747 B1 | 9/2002 | Decoster | |
| 7,942,937 B2* | 5/2011 | Brun | A61K 8/891 8/405 |
| 2003/0229947 A1* | 12/2003 | Clarke | A61K 8/4926 8/405 |
| 2006/0117496 A1* | 6/2006 | Bolton | A61Q 5/10 8/405 |
| 2013/0149358 A1 | 6/2013 | Colaco et al. | |
| 2013/0164240 A1 | 6/2013 | Schrott | |
| 2013/0233333 A1* | 9/2013 | Roulet | A61Q 5/04 132/204 |
| 2014/0044656 A1* | 2/2014 | Goralczyk | A61Q 17/04 424/59 |
| 2014/0044762 A1 | 2/2014 | Colaco et al. | |
| 2015/0093422 A1 | 4/2015 | Garrison et al. | |
| 2015/0322366 A1* | 11/2015 | Santucci-Aribert | B05D 5/08 206/438 |
| 2019/0254954 A1* | 8/2019 | Jegou | A61K 8/899 |

FOREIGN PATENT DOCUMENTS

| | | |
|---|---|---|
| EP | 0 780 422 A2 | 6/1997 |
| WO | WO 93/23446 A2 | 11/1993 |
| WO | WO 2012/042019 A2 | 4/2012 |
| WO | WO 2015/061048 A1 | 4/2015 |

OTHER PUBLICATIONS

International Search Report issued Jun. 18, 2018 in PCT/EP2018/059038 filed Apr. 9, 2018.
Schlossman, M. L., "Treated Pigments New Ways to Impart Color on the Skin," Cosmetics & Toiletries, vol. 105, Feb. 1990, 7 pages.
International Search Report issued Aug. 11, 2017 in International Application No. PCT/EP2017/065544, filed Jun. 23, 2017, citing documents AB-AD, AO, AP, and AX therein, 4 pages.
"Moisturizing Conditioner," Mintel online database, product information sheet for CHI Ionic Color Protector System From Farouk Systems, <www.gnpd.com>, Aug. 2010, XP-002765157, 3 pages.

* cited by examiner

*Primary Examiner* — David J Blanchard
*Assistant Examiner* — Edwin Coleman Mitchell
(74) *Attorney, Agent, or Firm* — Womble Bond Dickinson (US) LLP

(57) ABSTRACT

The present invention relates to a composition intended for dyeing keratin fibres, in particular of human keratin fibres such as the hair, comprising one or more acrylate-functionalized polymers and one or more silicones chosen from silicones functionalized with one or more mercapto groups, amino silicones, and mixtures thereof, and one or more pigments.

19 Claims, No Drawings

PROCESS FOR DYEING HAIR COMPRISING AT LEAST ONE PIGMENT, AT LEAST ONE ACRYLATE-FUNCTIONALIZED POLYMER AND AT LEAST ONE FUNCTIONALIZED SILICONE CHOSEN FROM SILICONES FUNCTIONALIZED WITH AT LEAST ONE MERCAPTO OR THIOL GROUP

The present invention relates to a process for dyeing keratin fibres, in particular of human keratin fibres such as the hair, comprising one or more pigments, to one or more acrylate-functionalized polymers and one or more silicones chosen from silicones functionalized with one or more mercapto groups, amino silicones, and mixtures thereof.

The invention also relates to a cosmetic process for treating keratin fibres, in which said fibres are treated with one or more compositions comprising one or more pigments, one or more acrylate-functionalized polymers and one or more silicones chosen from silicones functionalized with one or more mercapto groups, amino silicones, and mixtures thereof.

Hair is generally damaged and embrittled by the action of external atmospheric agents such as light and bad weather, and also by mechanical or chemical treatments, such as brushing, combing, dyeing, bleaching, permanent-waving and/or relaxing.

In the field of dyeing of keratin fibres, it is already known practice to dye keratin fibres via various techniques using direct dyes for non-permanent dyeing or dye precursors for permanent dyeing.

Non-permanent dyeing or direct dyeing consists in dyeing keratin fibres with dye compositions containing direct dyes. These dyes are coloured and colouring molecules that have affinity for keratin fibres. They are applied to the keratin fibres for the time required to obtain the desired colouring, and are then rinsed out.

The standard dyes that are used are, in particular, dyes of the nitrobenzene, anthraquinone, nitropyridine, azo, xanthene, acridine, azine or triarylmethane type, or natural dyes.

Some of these dyes may be used under lightening conditions, which enables the production of colourings that are visible on dark hair.

It is also known practice to dye keratin fibres permanently via oxidation dyeing. This dyeing technique consists in applying to the keratin fibres a composition containing dye precursors such as oxidation bases and couplers. These precursors, under the action of an oxidizing agent, form one or more coloured substances in the hair.

The variety of molecules used as oxidation bases and couplers allows a wide range of colours to be obtained, and the colourings resulting therefrom are generally permanent, strong and resistant to external agents, especially to light, bad weather, washing, perspiration and rubbing.

In order to be visible on dark hair, these two dyeing techniques require prior or simultaneous bleaching of the keratin fibres. This bleaching step, performed with an oxidizing agent such as hydrogen peroxide or persalts, results in appreciable degradation of the keratin fibres, which impairs their cosmetic properties. The hair then has a tendency to become coarse, more difficult to disentangle and more brittle.

Another dyeing method consists in using, pigments. Specifically, the use of pigment at the surface of the keratin fibres generally makes it possible to obtain visible colourings on dark hair, since the surface pigment masks the natural colour of the fibre. The use of pigment for dyeing keratin fibres is described, for example, in patent application FR 2 741 530, which recommends using for the temporary dyeing of keratin fibres a composition comprising at least one dispersion of film-forming polymer particles comprising at least one acid function and at least one pigment dispersed in the continuous phase of said dispersion.

The colourings obtained via this dyeing method have the drawback of being removed from the very first shampoo wash.

It is moreover known practice from patent application FR 2 907 678 to perform coloured coating of the hair using a composition comprising a polysiloxane/polyurea block copolymer and a pigment. However, with such a composition, the coatings obtained are not always very homogeneous and the individualization of the hair strands is not always very good.

It is also known practice from patent EP 1 392 222 to use a cosmetic composition for caring for and/or treating keratin materials, comprising a supramolecular polymer bearing a polymer backbone and at least two groups that are capable of forming at least three hydrogen bonds, and from patent EP 1 435 900 to use a hair composition comprising a supramolecular polymer comprising a polymer backbone and at least two groups that are capable of forming at least three hydrogen bonds and a surfactant or hair-conditioning agent.

Thus, the aim of the present invention is to provide a composition for dyeing keratin fibres, such as the hair, which can produce coloured coatings that show good resistance to attacking factors such as brushing, do not leach, are resistant to sweat, light and bad weather, and are persistent with respect to shampooing and the various attacking factors to which the hair may be subjected, without degradation of the keratin fibres and while at the same time conserving perfectly individualized hair strands.

This aim is achieved by the present invention, one subject of which is especially a composition comprising (i) one or more acrylate-functionalized polymers and (ii) one or more silicones chosen from silicones functionalized with one or more mercapto groups, amino silicones, and mixtures thereof and (iii) one or more pigments.

The composition according to the invention makes it possible to color keratin fibres satisfactorily, especially improving the color fastness, disentangling and the soft feel, and doing so in a long-lasting manner.

Thus, the composition according to the invention makes it possible to give keratin fibres satisfactory dyeing properties with shampoo-resistant properties.

In particular, the composition according to the invention makes it possible to afford improved dyeing properties even after five shampoos, relative to a composition comprising an acrylate-functionalized polymer or a silicone functionalized with one or more mercapto groups.

A subject of the invention is also a keratin fiber dyeing process, specifically hair dyeing process in which said fibres are treated with one or more compositions containing, taken together or separately in said composition(s), the following ingredients:

One or more pigments,
one or more acrylate-functionalized polymers,
one or more silicones chosen from silicones functionalized with one or more mercapto groups, amino silicones, and mixtures thereof.

The process thus makes it possible to color keratin fibres satisfactorily and in a long-lasting manner.

Another subject of the present invention concerns the use of the composition as defined previously for the keratin fibre dyeing, in particular human keratin fibres such as the hair.

The invention also relates to a multi-compartment device comprising at least a first compartment containing a composition comprising one or more acrylate-functionalized polymers and a second compartment containing one or more silicones chosen from silicones functionalized with one or more mercapto groups, amino silicones, and mixtures thereof, at least one of the compartment comprising one or more pigments.

Other characteristics and advantages of the invention will emerge more clearly on reading the description and the examples that follow.

In that which follows and unless otherwise indicated, the limits of a range of values are included within this range, in particular in the expressions "of between" and "ranging from . . . to . . . ".

As indicated above, the composition according to the invention comprises (i) one or more acrylate-functionalized polymers, this acrylate-functionalized polymer being an acrylate polymer comprising a reactive acrylate function that is capable of reacting, this acrylate function being able to be represented by CH2=CH—C(=O)—O—R, R being a divalent radical linking the reactive acrylate function to the polymer backbone.

Preferably, this acrylate-functionalized polymer(s) being an acrylate polymer comprising a reactive acrylate function that is capable of reacting, this acrylate function is represented by CH2=CH—C(=O)—O—R, R being a divalent radical linking the reactive acrylate function to the polymer backbone.

More preferentially, the acrylate-functionalized polymer(s) is or are chosen from acrylate-functionalized polyesters, acrylate-functionalized polyurethanes and acrylate-functionalized silicone polymers.

More preferentially still, the acrylate-functionalized polymer(s) is or are chosen from acrylate-functionalized silicone polymers.

Throughout the text hereinbelow, the term "silicone" is intended to denote, in accordance with what is generally accepted, any organosilicon polymer or oligomer of linear or cyclic, branched or crosslinked structure, of variable molecular weight, obtained by polymerization and/or polycondensation of suitably functionalized silanes, and constituted essentially of a repetition of main units in which the silicon atoms are linked together via oxygen atoms (siloxane bond —Si—O—Si—), optionally substituted hydrocarbon-based radicals being directly linked via a carbon atom to said silicon atoms. The hydrocarbon-based radicals that are the most common are alkyl radicals, especially of $C_1$-$C_{10}$, and in particular methyl, fluoroalkyl radicals, the alkyl part of which is of $C_1$-$C_{10}$, and aryl radicals and in particular phenyl.

The acrylate-functionalized silicone polymer(s) comprise a polysiloxane portion and a portion constituted of a non-silicone organic chain comprising one or more acrylate reactive groups; the non-silicone portion being grafted onto said polysiloxane portion in a side or end position.

Thus, the portion constituted of a non-silicone organic chain comprising one or more acrylate reactive groups is grafted onto the main chain of the polymer constituted by the polysiloxane portion.

Preferably, the acrylate-functionalized silicone polymer(s) is or are chosen from acrylate-functionalized silicone homopolymers and acrylate-fictionalized silicone copolymers.

More preferentially, the acrylate-functionalized silicone polymer(s) is or are chosen from acrylate-functionalized silicone copolymers, in particular copolymers comprising in their structure at least one acrylate-functionalized silicone unit and at least one dimethylsiloxane unit.

Preferably, the acrylate-functionalized silicone polymer(s) is or are a polymer of formula (I) or (II) below:

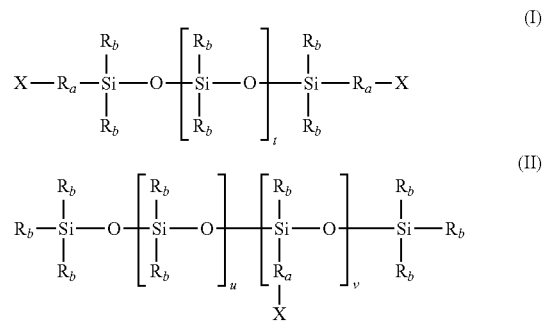

in which:

$R_a$ denotes a saturated or unsaturated, linear or branched, optionally cyclic, hydrocarbon-based chain comprising from 1 to 100 carbon atoms, optionally interrupted with a heteroatom chosen from N, O, S and P.

$R_a$ preferably denotes a $C_1$-$C_{100}$ alkylene group, better still a propylene group, $R_b$ denotes an alkyl group containing from 1 to 6 carbon atoms or an alkoxy group containing from 1 to 6 carbon atoms.

$R_b$ preferably denotes a methyl group or a methoxy group, t ranges from 0 to 132, and u ranges from 1 to 132, v ranges from 1 to 132, X represents an acrylate group.

According to a particular embodiment, X represents an acrylate group $R'_a O(C=O)C(R')=CH_2$ with $R'_a$ corresponding to a $C_1$-$C_{20}$ and preferably $C_1$-$C_5$ alkylene group, and R' represents a $C_1$-$C_{10}$ alkylene group.

In particular, the acrylate-functionalized silicone polymer(s) is or are a polymer of formula (III) below:

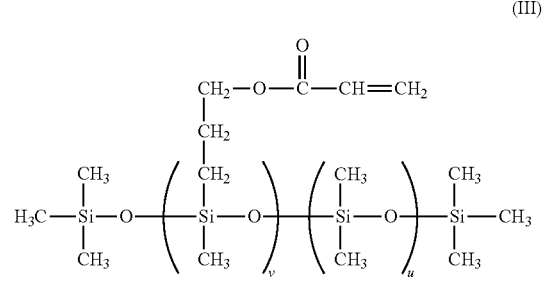

in which u and v have the same definition as those indicated in formulae (I) and (II) described previously.

Even more preferentially, the acrylate-functionalized polymer(s) is or are chosen from acryloxypropylmethylsiloxane polymers, especially the product sold under the trade name UMS-992 by the company Gelest, and copolymers of dimethylsiloxane and of acryloxypropylmethylsiloxane, especially the product sold under the trade name UMS-182R by the company Gelest.

Preferably, the acrylate-functionalized polymer is the polymer of formula (III) described previously comprising from 15 to 50 mol % of acryloxypropylmethylsiloxane.

The acrylate-functionalized polymer(s) may be present in the composition according to the invention in a content which may range from 0.1% to 20% by weight, preferably in a content ranging from 0.5% to 10% by weight relative to the total weight of the composition.

As indicated above, the composition according to the invention comprises (ii) one or more silicones chosen from silicones functionalized with one or more mercapto groups, amino silicones, and mixtures thereof.

Preferably, the silicone(s) (ii) is or are chosen from silicones functionalized with one or more mercapto groups.

Preferentially, the silicone(s) functionalized with one or more mercapto groups have a molecular weight preferably less than 1000.

The silicone(s) functionalized with one or more mercapto groups according to the invention may be chosen from the compounds having the following formulae:

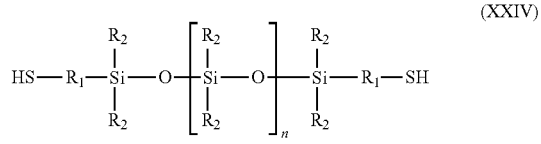

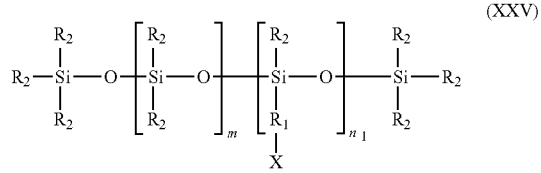

in which:

$R_1$ denotes a saturated or unsaturated, linear or branched, optionally cyclic, hydrocarbon-based chain comprising from 1 to 100 carbon atoms, optionally interrupted with a heteroatom chosen from N, O, S and P.

$R_1$ preferably denotes a $C_1$-$C_{100}$ alkylene group, better still a propylene group, $R_2$ denotes an alkyl group containing from 1 to 6 carbon atoms or an alkoxy group containing from 1 to 6 carbon atoms.

$R_2$ preferably denotes a methyl group or a methoxy group.

n ranges from 0 to 132, and $n_1$ ranges from 1 to 132 m ranges from 1 to 132.

Preferably, the functionalized silicone(s) used in the present invention is or are chosen from the silicones of formula (XXIV).

As functionalized silicones used in the present invention, mention may be made of the mercaptosiloxane in which the mercapto functions are at the chain ends, sold by the company Shin-Etsu under the reference X-22-167B, and the mercaptosiloxane in which the mercapto functions are pendent, sold by the company Shin-Etsu under the reference KF-2001.

Preferably, the silicone functionalized with one or more mercapto groups is a mercaptosiloxane polymer of formula XXV in which the mercapto functions are pendent. According to a particular embodiment, the group R in formula XXV is a C3H6 alkylene group and the group R2 is a methyl radical.

The functionalized silicone(s) may be introduced into the composition(s) either in pure form or in the presence of one or more silicone-based or hydrocarbon-based solvents, or in the form of a latex.

Preferably, the silicone(s) (ii) is or are chosen from amino silicones.

The term "amino silicone" means any polyaminosiloxane, i.e. any polysiloxane comprising at least one primary, secondary or tertiary amine function or a quaternary ammonium group.

The amino silicone(s) used according to the present invention is or are chosen from:

(a) the compounds corresponding to formula (XVII) below:

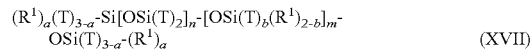

in which:

T is a hydrogen atom or a phenyl, hydroxyl (—OH) or $C_1$-$C_8$ alkyl radical, and preferably methyl, or a $C_1$-$C_8$ alkoxy, preferably methoxy, a denotes the number 0 or an integer from 1 to 3 and preferably 0, b denotes 0 or 1, and in particular 1, m and n are numbers such that the sum (n+m) can range especially from 1 to 2000 and in particular from 50 to 150, it being possible for n to denote a number from 0 to 1999 and in particular from 49 to 149, and for m to denote a number from 1 to 2000 and in particular from 1 to 10;

$R_1$ is a monovalent radical of formula —$C_qH2_qL$ in which q is a number from 2 to 8 and L is an amino group chosen from the following groups:

—N($R^2$)—$CH_2$—$CH_2$—N($R^2$)$_2$;
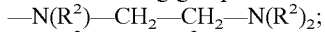
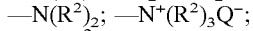
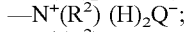
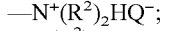

in which $R^2$ denotes a hydrogen atom, a phenyl, a benzyl or a saturated monovalent hydrocarbon-based radical, for example a $C_1$-$C_{20}$ alkyl radical, and $Q^-$ represents a halide ion, for instance fluoride, chloride, bromide or iodide.

In particular, the amino silicones corresponding to the definition of formula (XVII) are chosen from the compounds corresponding to formula (XVIII) below:

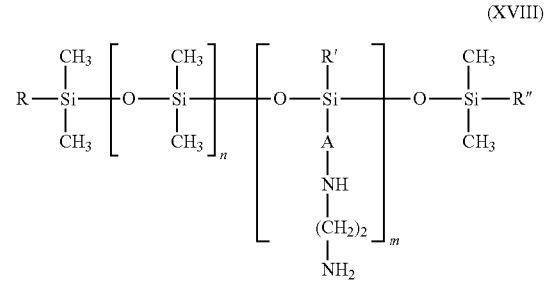

in which R, R' and R", which may be identical or different, denote a $C_1$-$C_4$ alkyl radical, preferably $CH_3$; a $C_1$-$C_4$ alkoxy radical, preferably methoxy; or OH; A represents a linear or branched, $C_3$-$C_8$ and preferably $C_3$-$C_6$ alkylene radical; m and n are integers dependent on the molecular weight and the sum of which is between 1 and 2000.

According to a first possibility, R, R' and R", which may be identical or different, represent a $C_1$-$C_4$ alkyl or hydroxyl radical, A represents a $C_3$ alkylene radical and m and n are such that the weight-average molecular mass of the compound is between 5000 and 500 000 approximately. Compounds of this type are referred to in the CTFA dictionary as "amodimethicones".

According to a second possibility, R, R' and R", which may be identical or different, represent a $C_1$-$C_4$ alkoxy or hydroxyl radical, at least one of the R or R" radicals is an alkoxy radical and A represents a $C_3$ alkylene radical. The hydroxyl/alkoxy molar ratio is preferably between 0.2/1 and 0.4/1 and advantageously equal to 0.3/1. Moreover, m and n are such that the weight-average molecular mass of the compound is between 2000 and $10^6$. More particularly, n is between 0 and 999 and m is between 1 and 1000, the sum of n and m being between 1 and 1000.

In this category of compounds, mention may be made, inter cilia, of the product Belsil® ADM 652 sold by Wacker.

According to a third possibility, R and R", which are different, represent a $C_1$-$C_4$ alkoxy or hydroxyl radical, at least one of the R and R" radicals is an alkoxy radical, R' represents a methyl radical and A represents a $C_3$ alkylene radical. The hydroxyl/alkoxy mole ratio is preferably between 1/0.8 and 1/1.1 and advantageously is equal to 1/0.95. Moreover, m and n are such that the weight-average molecular mass of the compound is between 2000 and 200 000. More particularly, n is between 0 and 999 and m is between 1 and 1000, the sum of n and m being between 1 and 1000.

More particularly, mention may be made of the product Fluid WR® 1300 sold by Wacker.

According to a fourth possibility, R and R" represent a hydroxyl radical, R' represents a methyl radical and A is a $C_4$-$C_5$ and preferably $C_4$ alkylene radical. Moreover, in and n are such that the weight-average molecular mass of the compound is between 2000 and $10^6$. More particularly, n is between 0 and 1999 and m is between 1 and 2000, the sum of n and m being between 1 and 2000.

A product of this type is especially sold under the name DC 28299 by Dow Corning.

It is noted that the molecular mass of these silicones is determined by gel permeation chromatography (room temperature, polystyrene standard, μ styragem columns, eluent THF, flow rate of 1 mm/minute, 200 μl of a solution containing 0.5% by weight of silicone in THF are injected, and detection is performed by refractometry and UV-metry).

A product corresponding to the definition of formula (VI) is in particular the polymer known in the CTFA dictionary (7th edition, 1997) as "trimethylsilyl amodimethicone", corresponding to formula (XIX) below:

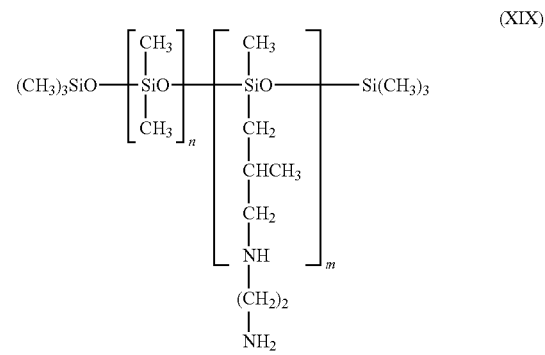

in which n and m have the meanings given above in accordance with formula (XVIII).

Such compounds are described, for example, in EP 0095238; a compound of formula (XIX) is sold, for example, under the name Q2-8220 by the company OSI.

(b) the compounds corresponding to formula (XX) below:

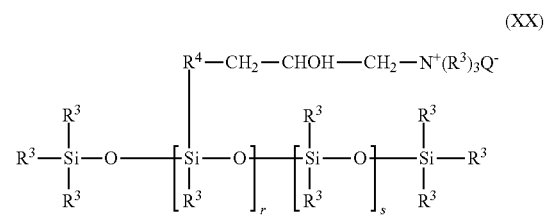

in which:

$R^3$ represents a monovalent $C_1$-$C_{18}$ hydrocarbon-based radical, and in particular a $C_1$-$C_{18}$ alkyl or $C_7$-$C_{18}$ alkenyl radical, for example methyl;

$R^4$ represents a divalent hydrocarbon-based radical, especially a $C_1$-$C_{18}$ alkylene radical or a divalent $C_1$-$C_{18}$, and for example $C_1$-$C_8$, alkyleneoxy radical;

$Q^-$ is a halide ion, especially chloride;

r represents a mean statistical value from 2 to 20 and in particular from 2 to 8;

s represents a mean statistical value from 20 to 200 and in particular from 20 to 50.

Such compounds are described more particularly in U.S. Pat. No. 4,185,087.

A compound falling within this class is the product sold by the company Union Carbide under the name Ucar Silicone ALE 56.

(c) the quaternary ammonium silicones of formula (XXI):

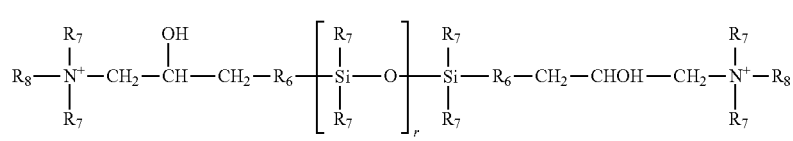

in which:

$R_7$, which may be identical or different, represents a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkyleneoxy radical linked to the Si via an SiC bond;

$R_8$, which may be identical or different, represents a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—NHCOR$_7$ radical;

$X^-$ is an anion such as a halide ion, especially chloride, or an organic acid salt (acetate, etc.);

r represents a mean statistical value from 2 to 200 and in particular from 5 to 100.

These silicones are described, for example, in patent application EP-A 0 530 974.

d) the amino silicones of formula (XXII) below:

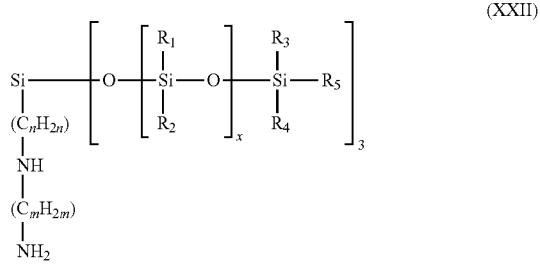

(XXII)

in which:

$R_1$, $R_2$, $R_3$ and $R_4$, which may be identical or different, denote a $C_1$-$C_4$ alkyl radical or a phenyl group, $R_5$ denotes a $C_1$-$C_4$ alkyl radical or a hydroxyl group, n is an integer ranging from 1 to 5, in is an integer ranging from 1 to 5, and in which x is selected such that the amine number is between 0.01 and 1 meq/g.

According to one embodiment, the amino silicone is a silicone having the following formula in which R is a cetearyl radical:

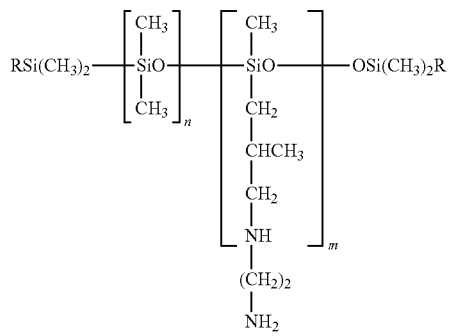

Preferably, the amino silicone(s) are non-quaternized amino silicones.

For the purposes of the present invention, the term "non-quaternized amino silicone" means an amino silicone not comprising a permanent cationic charge, i.e. quaternized ammonium groups.

In other words, the non-quaternized amino silicone(s) comprise in their structure at least one primary, secondary or tertiary amine function but do not comprise a quaternary ammonium function.

The silicone(s) functionalized with an amino or mercapto group may be present in the composition according to the invention in a content which may range from 0.1% to 10% by weight and preferably in a content ranging from 0.2% to 5% by weight relative to the total weight of the composition.

Pigments

The composition that is useful in the process of the invention comprises at least one pigment. The term "pigment" means any pigment that gives colour to keratin materials. Their solubility in water at 25° C. and atmospheric pressure (760 mmHg) is less than 0.05% by weight, preferably less than 0.01%.

The pigments that may be used are chosen especially from the organic and/or mineral pigments known in the art, especially those described in Kirk-Othmer's chemical technology Encyclopaedia and in Ullmann's industrial chemistry encyclopaedia.

These pigments may be in the form of powder or of pigmentary paste, They may be coated or uncoated.

The pigments may be chosen, for example, from mineral pigments, organic pigments, lakes, pigments with special effects such as nacres or glitter flakes, and mixtures thereof.

The pigment may be a mineral pigment. The term "mineral pigment" means any pigment that satisfies the definition in Ullmann's encyclopaedia in the chapter on inorganic pigments. Among the mineral pigments that are useful in the present invention, mention may be made of iron oxides, chromium oxides, manganese violet, ultramarine blue, chromium hydrate, ferric blue and titanium oxide.

The pigment may be an organic pigment. The term "organic pigment" means any pigment that satisfies the definition in Ullmann's encyclopaedia in the chapter on organic pigments. The organic pigment may be chosen especially from nitroso, nitro, azo, xanthene, quinoline, anthraquinone, phthalocyanin, metal-complex, isoindolinone, isoindoline, quinacridone, perinone, perylene, diketopyrrolopyrrole, thioindigo, dioxazine, triphenylmethane and quinophthalone compounds.

In particular, the white or coloured organic pigments may be chosen from carmine, carbon black, aniline black, azo yellow, quinacridone, phthalocyanin blue, sorghum red, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, and the pigments obtained by oxidative polymerization of indole or phenolic derivatives as described in patent FR 2 679 771.

The pigments in accordance with the invention may also be in the form of composite pigments as described in patent EP 1 184 426. These composite pigments may be compounds especially of particles comprising a mineral core, at least one binder for ensuring the binding of the organic pigments to the core, and at least one organic pigment at least partially covering the core.

The organic pigment may also be a lake. The term "lake" means dyes adsorbed onto insoluble particles, the assembly thus obtained remaining insoluble during use.

The inorganic substrates onto which the dyes are adsorbed are, for example, alumina, silica, calcium sodium borosilicate or calcium aluminium borosilicate, and aluminium.

Among the dyes, mention may be made of cochineal carmine. Mention may also be made of the dyes known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 10 (CI 77 002), D&C Green 3 (CI 42 053), D&C Blue 1 (CI 42 090).

An example of a lake that may be mentioned is the product known under the following name: D&C Red 7 (CI 15 850:1).

The pigment may also be a pigment with special effects. The term "pigments with special effects" means pigments that generally create a non-uniform coloured appearance (characterized by a certain shade, a certain vivacity and a certain lightness) that changes as a function of the conditions of observation (light, temperature, observation angles, etc.). They thus contrast with colored pigments that afford a standard uniform opaque, semi-transparent or transparent shade.

Several types of pigment with special effects exist: those with a low refractive index, such as fluorescent, photochromic or thermochromic pigments, and those with a higher refractive index, such as nacres or glitter flakes.

Examples of pigments with special effects that may be mentioned include nacreous pigments such as titanium mica coated with an iron oxide, mica coated with an iron oxide, mica coated with bismuth oxychloride, titanium mica coated with chromium oxide, titanium mica coated with an organic dye especially of the abovementioned type, and also nacreous pigments based on bismuth oxychloride. They may also be mica particles at the surface of which are superposed at least two successive layers of metal oxides and/or of organic dyestuffs.

The nacres may more particularly have a yellow, pink, red, bronze, orange, brown, gold and/or coppery colour or tint.

Nacres that may be used within the context of the present invention, by way of illustration, and that may especially be mentioned include the gold-coloured nacres sold especially by the company Engelhard under the name Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona), by the company Eckart under the name Prestige Bronze and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper tint sold especially by the company Engelhard under the name Copper 340A (Timica) and by the company Eckart under the name Prestige Copper; the nacres with a red tint sold especially by the company Merck under the name Sienna fine (17386) (Colorona); the nacres with a yellow tint sold especially by the company Engelhard under the name Yellow (4502) (Chromalite); the red nacres with a gold tint sold especially by the company Engelhard under the name Sunstone G012 (Gemtone); the black nacres with a gold tint sold especially by the company Engelhard under the name Nu antique bronze 240 AB (Timica), the blue nacres sold especially by the company Merck under the name Matte blue (17433) (Microna), Dark Blue (117324) (Colorona), the white nacres with a silvery tint sold especially by the company Merck under the name Xirona Silver, and the golden-green pink-orange nacres sold especially by the company Merck under the name Indian summer (Xirona), and mixtures thereof.

In addition to nacres on a mica support, multilayer pigments based on synthetic substrates such as alumina, silica, sodium calcium borosilicate or calcium aluminium borosilicate, and aluminium, may be envisaged.

Mention may also be made of pigments with an interference effect that are not fixed onto a substrate, for instance liquid crystals (Helicones HC from Wacker), holographic interference glitter flakes (Geometric Pigments or Spectra f/x from Spectratek). Pigments with special effects also comprise fluorescent pigments, whether these are substances that are fluorescent in daylight or that produce an ultraviolet fluorescence, phosphorescent pigments, photochromic pigments, thermochromic pigments and quantum dots, sold, for example, by the company Quantum Dots Corporation.

The variety of pigments that may be used in the present invention makes it possible to obtain a wide range of colours, and also particular optical effects such as metallic effects or interference effects.

The size of the pigment used in the cosmetic composition according to the present invention is generally between 10 nm and 200 preferably between 20 nm and 80 µm and more preferentially between 30 nm and 50 µm.

The pigments may be dispersed in the product by means of a dispersant.

The dispersant serves to protect the dispersed particles against agglomeration or flocculation thereof. This dispersant may be a surfactant, an oligomer, a polymer or a mixture of several thereof, bearing one or more functionalities with strong affinity for the surface of the particles to be dispersed. In particular, they can physically or chemically attach to the surface of the pigments. These dispersants also contain at least one functional group that is compatible with or soluble in the continuous medium. In particular, 12-hydroxystearic acid esters and in particular $C_8$ to $C_{20}$ fatty acid esters of polyols such as glycerol or diglycerol are used, such as poly(12-hydroxystearic acid) stearate with a molecular weight of about 750 g/mol, such as the product sold under the name Solsperse 21 000 by the company Avecia, polyglyceryl-2 dipolyhydroxystearate (CTFA name) sold under the reference Dehymyls PGPH by the company Henkel, or polyhydroxystearic acid such as the product sold under the reference Arlacel P100 by the company Uniqema, and mixtures thereof.

As other dispersants that may be used in the compositions of the invention, mention may be made of quaternary ammonium derivatives of polycondensed fatty acids, for instance Solsperse 17 000 sold by the company Avecia, and polydimethylsiloxane/oxypropylene mixtures such as those sold by the company Dow Corning under the references DC2-5185 and DC2-5225 C.

The pigments that are used in the cosmetic composition according to the invention may be surface-treated with an organic agent.

Thus, the pigments that have been surface-treated beforehand, which are useful in the context of the invention, are pigments that have totally or partially undergone a surface treatment of chemical, electronic, electrochemical, mechanochemical or mechanical nature, with an organic agent such as those described especially in Cosmetics and Toiletries, February 1990, Vol. 105, pp. 53-64, before being dispersed in the composition in accordance with the invention. These organic agents may be chosen, for example, from amino acids; waxes, for example carnauba wax and beeswax; fatty acids, fatty alcohols and derivatives thereof, such as stearic acid, hydroxystearic acid, stearyl alcohol, hydroxystearyl alcohol and lauric acid and derivatives thereof; anionic surfactants; lecithins; sodium, potassium, magnesium, iron, titanium, zinc or aluminium salts of fatty acids, for example aluminium stearate or laurate; metal alkoxides; polysaccharides, for example chitosan, cellulose and derivatives thereof; polyethylene; (meth)acrylic polymers, for example polyinethyl methacrylates; polymers and copolymers containing acrylate units; proteins; alkanolamines; silicone compounds, for example silicones, polydimethylsiloxanes, alkoxysilanes, alkylsilanes and siloxysilicates; organofluorine compounds, for example perfluoroalkyl ethers; fluorosilicone compounds.

The surface-treated pigments that are useful in the cosmetic composition according to the invention may also have been treated with a mixture of these compounds and/or may have undergone several surface treatments.

The surface-treated pigments that are useful in the context of the present invention may be prepared according to surface-treatment techniques that are well known to those skilled in the art, or may be commercially available in the required form.

Preferably, the surface-treated pigments are coated with an organic layer.

The organic agent with which the pigments are treated may be deposited on the pigments by evaporation of solvent, chemical reaction between the molecules of the surface agent or creation of a covalent bond between the surface agent and the pigments.

The surface treatment may thus be performed, for example, by chemical reaction of a surface agent with the surface of the pigments and creation of a covalent bond between the surface agent and the pigments or the fillers. This method is especially described in U.S. Pat. No. 4,578,266.

An organic agent covalently bonded to the pigments will preferably be used.

The agent for the surface treatment may represent from 0.1% to 50% by weight, preferably from 0.5% to 30% by weight and even more preferentially from 1% to 10% by weight relative to the total weight of the surface-treated pigments.

Preferably, the surface treatments of the pigments are chosen from the following treatments:
- a PEG-silicone treatment, for instance the AQ surface treatment sold by LCW;
- a chitosan treatment, for instance the CTS surface treatment sold by LCW;
- a triethoxycaprylylsilane treatment, for instance the AS surface treatment sold by LCW;
- a methicone treatment, for instance the SI surface treatment sold by LCW;
- a dimethicone treatment, for instance the Covasil 3.05 surface treatment sold by LCW;
- a dimethicone/trimethyl siloxysilicate treatment, for instance the Covasil 4.05 surface treatment sold by LCW
- a lauroyllysine treatment, for instance the LL surface treatment sold by LCW;
- a lauroglysine dimethicone treatment, for instance the LL/SI surface treatment sold by LCW;
- a magnesium myristate treatment, for instance the MM surface treatment sold by LCW;
- an aluminium dimyristate treatment, for instance the MI surface treatment sold by Miyoshi;
- a perfluoropolymethylisopropyl ether treatment, for instance the FHC surface treatment sold by LCW;
- an isostearyl sebacate treatment, for instance the HS surface treatment sold by Miyoshi;
- a disodium stearoyl glutamate treatment, for instance the NAI surface treatment sold by Miyoshi;
- a dimethicone/disodium stearoyl glutamate treatment, for instance the SA/NAI surface treatment sold by Miyoshi;
- a perfluoroalkyl phosphate treatment, for instance the PF surface treatment sold by Daito;
- an acrylate/dimethicone copolymer and perfluoroalkyl phosphate treatment, for instance the FSA surface treatment sold by Daito;
- a polymethylhydrogen siloxane/perfluoroalkyl phosphate treatment, for instance the FSDI surface treatment sold by Daito;
- a lauryl lysine/aluminium tristearate treatment, for instance the LL-StAI surface treatment sold by Daito;
- an octyltriethylsilane treatment, for instance the OTS surface treatment sold by Daito;
- an octyltriethylsilane/perfluoroalkyl phosphate treatment, for instance the FOTS surface treatment sold by Daito;
- an acrylate/dimethicone copolymer treatment, for instance the ASC surface treatment sold by Daito;
- an isopropyl titanium triisostearate treatment, for instance the ITT surface treatment sold by Daito;
- a microcrystalline cellulose and carboxymethylcellulose treatment, for instance the AC surface treatment sold by Daito;
- a cellulose treatment, for instance the C2 surface treatment sold by Daito;
- an acrylate copolymer treatment, for instance the APD surface treatment sold by Daito;
- a perfluoroalkyl phosphate/isopropyl titanium triisostearate treatment, for instance the PF+ITT surface treatment sold by Daito.

The composition in accordance with the present invention may moreover comprise one or more surface-untreated pigments.

According to a particular embodiment of the invention, the pigment(s) are mineral pigments.

According to another particular embodiment of the invention, the pigment(s) are chosen from nacres.

The amount of pigments may range from 0.5% to 40% and preferably from 1% to 20%.

The vehicle of the composition according to the invention may comprise water and/or organic solvents. Organic solvents that may be mentioned include non-fatty alcohols such as ethyl alcohol, isopropyl alcohol, benzyl alcohol and phenylethyl alcohol, or polyols or polyol ethers, for instance glycerol, ethylene glycol monomethyl, monoethyl or monobutyl ether, propylene glycol or ethers thereof, for instance propylene glycol monomethyl ether, butylene glycol, dipropylene glycol, and also diethylene glycol alkyl ethers, for instance diethylene glycol monoethyl ether or monobutyl ether.

The organic solvent may be a fatty substance, which is preferably liquid. The liquid fatty substances preferably have a viscosity of less than or equal to 2 Pa·s, better still less than or equal to 1 Pa·s and even better still less than or equal to 0.1 Pa·s at a temperature of 25° C. and at a shear rate of 1 s$^{-1}$.

These fatty substances may be chosen from hydrocarbons composed solely of carbon and hydrogen atoms, fatty alcohols, for example
- linear or branched, optionally cyclic, $C_6$-$C_{16}$ alkanes. Examples that may be mentioned include hexane, undecane, dodecane, tridecane, and isoparaffins, for instance isohexadecane, isododecane and dodecane,
- linear or branched hydrocarbons of mineral, animal or synthetic origin with more than 16 carbon atoms, such as volatile or non-volatile liquid paraffins and derivatives thereof, petroleum jelly, liquid petroleum jelly, polydecenes, hydrogenated polyisobutene such as the product sold under the brand name Parleam® by the company NOF Corporation, and squalane,
- saturated liquid fatty alcohols chosen from octyldodecanol, isostearyl alcohol and 2-hexyldecanol.

The medium of the composition according to the invention may be a dispersed medium, especially dispersed in isododecane, an emulsion in water or an ethanol/water mixture.

The composition used according to the invention may be, independently of each other, in the form of a lotion, a gel, a mousse, a cream or a paste.

According to one embodiment, the composition according to the invention comprises one or more acrylate-functionalized silicone polymers and one or more silicones functionalized with one or more mercapto groups.

According to another embodiment, the composition according to the invention comprises one or more pigments, one or more acrylate-functionalized silicone polymers and one or more amino silicones.

According to another embodiment, the composition according to the invention comprises one or more pigments, one or more acrylate-functionalized silicone polymers, one or more silicones functionalized with one or more mercapto groups and one or more amino silicones.

Preferably, the composition according to the invention comprises one or more pigments, one or more acrylate-functionalized silicone polymers and one or more silicones functionalized with one or more mercapto groups.

More preferentially, the composition according to the invention comprises (i) one or more acrylate-functionalized polymers chosen from acrylate-functionalized silicone copolymers obtained by polymerization from a mixture of monomers comprising at least one monomer of formula (I) or (II) and at least one dimethylsiloxane monomer and (ii) one or more functionalized silicones chosen from the silicones of formula (XXIV) and (iii) one or more pigments.

Even more preferentially, the acrylate-functionalized silicone copolymers are obtained by polymerization from a mixture of monomers comprising at least one monomer of formula (III).

The present invention also relates to the use of said composition for dyeing keratin fibres, in particular human keratin fibres such as the hair.

A subject of the invention is also a cosmetic process for dyeing keratin fibres, in particular human keratin fibres such as the hair, in which said fibres are treated with one or more compositions containing, taken together or separately in said composition(s), the following ingredients:
- one or more pigments,
- one or more acrylate-functionalized polymers,
- one or more silicones chosen from silicones functionalized with one or more mercapto groups, amino silicones, and mixtures thereof.

The acrylate-functionalized polymer(s) and the functionalized silicones are as defined previously.

Preferably, the acrylate-functionalized polymer(s) is or are chosen from acrylate-functionalized silicone polymers, in particular acrylate-functionalized silicone copolymers.

Preferably, the process according to the invention comprises a step of applying to said fibres a composition comprising one or more acrylate-functionalized polymers, one or more silicones chosen from silicones functionalized with one or more mercapto groups, amino silicones, and mixtures thereof, and one or more pigments.

Alternatively, the process according to the invention comprises (a) a step of applying to said fibres a composition comprising one or more acrylate-functionalized polymers and (b) a step of applying to said fibres a composition comprising one or more silicones chosen from silicones functionalized with one or more mercapto groups, amino silicones, and mixtures thereof, at least one of the composition of step (a) or (b) contains one or more pigments.

According to this alternative, step (a) may be performed before step (b) or vice versa.

The leave-on time of the composition or of each of the compositions defined above may be between 3 minutes and 1 hour.

The treatment process according to the invention may or may not be rinsed out.

The keratin fibres may be heated in the course of the process according to the invention at least to a temperature ranging from 40° C. to 210° C.

Preferably, the keratin fibres are heated after the application of the acrylate-functionalized polymer(s) and of the functionalized silicone(s).

According to one embodiment, the process according to the invention comprises:
  (a) a step of applying to said fibres a composition comprising one or more acrylate-functionalized polymers, and
  (b) a step of applying to said fibres a composition comprising one or more silicones chosen from silicones functionalized with one or more mercapto groups, amino silicones, and mixtures thereof,
  at least one of said compositions comprising one or more pigments, and
  (c) at least one step of heating the keratin fibres to a temperature ranging from 40° C. to 210° C. performed after steps (a) and (b).

In accordance with this embodiment, the process according to the invention may comprise two steps of heating of the keratin fibres.

According to one embodiment, the process comprises a step of heating the keratin fibres to a temperature ranging from 40° C. to 60° C. and a step of heating the keratin fibres to a temperature ranging from 100° C. to 210° C. by means of a heat source.

In practice, this operation may be performed using a hairstyling hood, a hairdryer, a round or flat iron, an infrared ray dispenser or other heating appliances. Preferably, the heat source is a straightening iron.

The process according to the invention may comprise a step of photochemical treatment of the keratin fibres in replacement for or in addition to the heating step as described previously.

Preferably, the photochemical treatment step is performed using a photoinitiator in an amount ranging from 1 to 20% by weight relative to the acrylate-functionalized polymer, especially the acrylate-functionalized silicone polymer.

More preferentially, the photoinitiator is 2,2-dimethoxy-2-phenylacetophenone.

According to a particular embodiment, the photoinitiator is a photoinitiator for UV.

The invention also relates to a multi-compartment device comprising a first compartment containing a composition comprising one or more acrylate-functionalized polymers and a second compartment containing one or more silicones chosen from silicones functionalized with one or more mercapto groups, amino silicones, and mixtures thereof.

Preferably, the device comprises a first compartment containing a composition comprising one or more acrylate-functionalized silicone polymers and a second compartment containing one or more silicones chosen from silicones functionalized with one or more mercapto groups, amino silicones, and mixtures thereof, at least one of the compartment comprising one or more pigments.

More preferentially, the device comprises a first compartment containing a composition comprising one or more acrylate-functionalized silicone polymers and a second compartment containing one or more silicones chosen from silicones functionalized with one or more mercapto groups, at least one of the compartment comprising one or more pigments.

Alternatively, the device comprises a first compartment containing a composition comprising one or more acrylate-functionalized silicone polymers and a second compartment comprising a composition containing one or more silicones chosen from silicones functionalized with one or more amino groups, at least one of the composition comprising one or more pigments.

Also alternatively, the device comprises a first compartment containing a composition comprising one or more acrylate-functionalized silicone polymers and a second compartment comprising a composition containing one or more silicones chosen from silicones functionalized with one or more amino groups and silicones functionalized with one or more mercapto groups, at least one of the composition comprising one or more pigments.

The following examples are given by way of illustration of the present invention.

EXAMPLES

The below data were generated from natural locks of hair with 90% of white hair. On 1 gram of lock was applied 0.5 g of dyeing composition.

The locks of hair were treated with the ingredients indicated in the table below:

Composition 5 (Comparison):

| Comparative composition 5 | Conc. |
|---|---|
| GLYCINE | 3% |
| PHENOXYETHANOL | 0.7% |
| DIVINYLDIMETHICONE/DIMETHICONE COPOLYMER (and) C12-13 PARETH-3 (and) C12-13 PARETH-23 (60% Active Material in an aqueous emulsion) | 8.3% |
| CAPRYLYL GLYCOL | 1% |
| MAGNESIUM ALUMINUM SILICATE | 1.1% |
| STYRENE/ACRYLATES/AMMONIUM METHACRYLATE COPOLYMER (and) SODIUM LAURETH SULFATE (and) CAPRYLYL GLYCOL (40% Active material in an aqueous emulsion 40%) | 21% |
| MICA (and) IRON OXIDES | 6% |
| water | q.s |

I. Evaluation Procedure

The compositions 1 to 4 described in the table above are applied to locks with a brush, then they were heated at 50° C. on a heating plate. After 1 hour at 50° C., the locks were treated with a straightening (10 times at 210° C.) and then left at 50° C. 1 hour more.

The locks are left to stand at room temperature for a time of 48 hours before performing a first color evaluation (measurement T0).

Then the locks were washed with water by soaking the locks in water for 1 hour. After 24 h a room temperature, the color was re evaluated (T1), then the color was evaluated after 2 shampoos and 24 h at room temperature (T2).

For the compositions 1 to 3, the color evaluation (T2) was conducted after 1 shampoo (most of the color was removed after 1 shampoo).

For composition 5, the composition was applied on a lock and left 30 min at 50° C.

The color evaluation was done with a spectrophotometer in the L*a*b* system wherein According to this system, L indicates the lightness. The lowest is the value of L, the most intense is the color of the hair. The chromaticity coordinates are expressed by the parameters a* and b*, a* indicating the axis of red/green shades and b the axis of yellow/blue shades.

| compositions | Ingredients (weight %) |
|---|---|
| 1 | Composition containing Acrylate-functionalized silicone polymer[2] 0.75% (active material), pigment[3] 6% and qs 100% isododecane |
| 2 | Composition containing Silicone functionalized with mercapto groups[1] 0.5% (active material), Pigment[3] 6%, q.s. 100% isododecane |
| 3 | Composition containing Bis-Cetearyl Amodimethicone 0.25% (active material), Pigments (3) 6%, q.s. 100% isododecane |
| 4a | Composition containing silicone functionalized with mercapto groups[1] 0.5% (active material) by weight and acrylate-functionalized silicone polymer[2] 0.75% (active material) by weight, pigments[3] 6% in weight, bis-cetearyl amodimethicone 3% (active material) by weight, q.s. 100% isododecane |
| 4b | Composition containing silicone functionalized with mercapto groups[1] 6% (active material) by weight and acrylate-functionalized silicone polymer[2] 9% (active material) by weight, pigments[3] 6% in weight, bis-cetearyl amodimethicone 3% (active material) by weight, q.s. 100% isododecane |

[1] sold under the name KF2001 by the company Shin-Etsu (formula XXV with R1 = $C_3H_6$ and R2 = $CH_3$)
[2] sold under the name UMS 182 by the company Gelest (formula (III))
[3] IRON OXIDES (and) MICA (pearlescent pigment sold by Eckart)

|         | L*   | a*   | b*   |
|---------|------|------|------|
| control | 63.1 | 0.8  | 16.9 |

| T0      | L*   | a*   | b*   |
|---------|------|------|------|
| control | 63.1 | 0.8  | 16.9 |
| 1       | 55.7 | 12.5 | 19.3 |
| 2       | 54.8 | 12.8 | 19.4 |
| 3       | 56.2 | 12.9 | 19.4 |

| T1 | L*   | a*    | b*   |
|----|------|-------|------|
| 1  | 56.6 | 10.02 | 19   |
| 2  | 55.0 | 11.6  | 18.7 |
| 3  | 57.0 | 12.2  | 19.4 |

| T2 | L*   | a*   | b*   |
|----|------|------|------|
| 1  | 61.0 | 3.8  | 16.9 |
| 2  | 61.7 | 4.3  | 17.8 |
| 3  | 62.2 | 3.6  | 17.0 |
| 4a | 53.1 | 12.2 | 19.7 |

These results show that alone, these silicone did not provide a color retention after shampooing.

|    | L*   | a*    | b*   |
|----|------|-------|------|
|    |      | T0    |      |
| 4b | 53.4 | 13.9  | 20.9 |
| 5  | 54.8 | 11.2  | 17.7 |
|    |      | T1    |      |
| 4b | 52.3 | 14.04 | 21.2 |
| 5  | 54.4 | 10.71 | 17.9 |
|    |      | T2    |      |
| 4b | 54.1 | 12.6  | 21.3 |
| 5  | 58.7 | 5.5   | 16.7 |

These results show that the composition of the invention exhibit an improved color fastness. Additionally, the lock treated with the composition of the invention is brighter and softer than the lock treated with the composition 5. With composition 4, there was no color transfert when rubbed with paper).

Compositions with a Photoinitiator

The locks of hair were treated with the ingredients indicated in the table below:

| compositions | Ingredients (weight %) |
|---|---|
| 1c | Composition containing Acrylate-functionalized silicone polymer(2) 9% (active material), Ethyl (2,4,6-trimethylbenzoyl) phenylphosphinate (photoinitiator) 0.9% pigment[3] 6% and qs 100% isododecane |
| 2c | Composition containing Silicone functionalized with mercapto groups[1] 6% (active material), Ethyl (2,4,6-trimethylbenzoyl) phenylphosphinate (photoinitiator) 0.9% Pigment[3] 6%, q.s. 100% isododecane |
| 3c | Composition containing Bis-Cetearyl Amodimethicone 3% (active material), Ethyl (2,4,6-trimethylbenzoyl) phenylphosphinate (photoinitiator) 0.9% Pigments[3] 6%, q.s. 100% isododecane |
| 4c | Composition containing silicone functionalized with mercapto groups[1] 6% (active material) and acrylate-functionalized silicone polymer[2] 9% (active material), Ethyl (2,4,6-trimethylbenzoyl) phenylphosphinate (photoinitiator) 0.9% pigments[3] 6% , bis-cetearyl amodimethicone** 3% (active material), q.s. 100% isododecane |

[1]sold under the name KF2001 by the company Shin-Etsu (formula XXV with R1 = C$_3$H$_6$ and R2 = CH$_3$)
[2]sold under the name UMS 182 by the company Gelest (formula (III))
[3]IRON OXIDES (and) MICA (pearlescent pigment sold by Eckart).

The compositions 1c to 4c described in the table above are applied to locks with a brush, then the locks were exposed to UV radiations (2×5 min).

The locks are left to stand at room temperature for a time of 48 hours before performing a first color evaluation (measurement T0).

Then the locks were washed with water by soaking the locks in water for 1 hour. After 24 h a room temperature, the color was re-evaluated (T1), then the color was evaluated after 2 shampoos and 24 h at room temperature (T2) and then after 5 shampoos and 24 h at room temperature for the composition of the invention.

For the compositions 1 b to 3b, the color evaluation (T2) was conducted after 1 shampoo (most of the color was removed after 1 shampoo).

For composition 5, the composition was applied on a lock and left 30 min at 50° C.

The color evaluation was conducted as disclosed in the previous examples. The L*a*b* results are reported in the table below:

|         | L*    | a*    | b*   |
|---------|-------|-------|------|
| control | 63.1  | 0.8   | 16.9 |
|         |       | T0    |      |
| 1b      | 53.9  | 14.4  | 19.9 |
| 2b      | 54.1  | 14.9  | 20.8 |
| 3b      | 53.07 | 14.13 | 19.7 |
|         |       | T1    |      |
| 1b      | 55.1  | 12.5  | 18.7 |
| 2b      | 54.0  | 13.9  | 20.3 |
| 3b      | 54.9  | 13.5  | 19.3 |
|         |       | T2    |      |
| 1b      | 58.4  | 3.0   | 14.3 |
| 2b      | 59.5  | 6.2   | 16.9 |
| 3b      | 58.5  | 5.0   | 15.7 |

These results show that alone, these silicones did not provide a color retention. Additionally, the water in which the locks 1c to 3c were soaked was colored whereas the water for the lock 4c remains uncoloured.

|   | L* | a* | b* |
|---|---|---|---|
| T0 | | | |
| 4 | 53.0 | 13.6 | 20.4 |
| 5 | 54.8 | 11.2 | 17.7 |
| T1 | | | |
| 4 | 52.7 | 14.3 | 20.3 |
| 5 | 54.4 | 10.7 | 17.9 |
| T2 | | | |
| 4 | 52.1 | 11.7 | 17.9 |
| 5 | 58.7 | 5.5 | 16.7 |
| T3 | | | |
| 4 | 55.1 | 12.7 | 20.0 |

These results show that the composition of the invention provide an improved color retention, still noticeable after 5 shampoo.

The invention claimed is:

1. A composition comprising:
   (i) one or more acrylate-functionalized polymers, wherein the one or more acrylate-functionalized polymer(s) is or are chosen from acrylate-functionalized silicone homopolymers and acrylate-functionalized silicone copolymers,
   (ii) one or more silicones functionalized with one or more mercapto groups, wherein the one or more silicone(s) functionalized with one or more mercapto groups is or are chosen from the compounds of the following formulae:

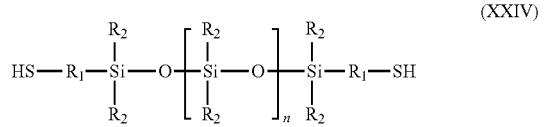

(XXIV)

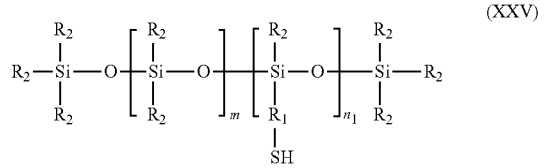

(XXV)

in which $R_1$ denotes a saturated or unsaturated, linear or branched, optionally cyclic, hydrocarbon-based chain comprising from 1 to 100 carbon atoms, optionally interrupted with a heteroatom chosen from N, O, S and P, $R_2$ denotes an alkyl group containing from 1 to 6 carbon atoms or an alkoxy group containing from 1 to 6 carbon atoms, n ranges from 0 to 132, $n_1$ ranges from 1 to 132, and m ranges from 1 to 132, and (iii) one or more pigments.

2. The composition according to claim 1, wherein the one or more acrylate-functionalized polymer(s) is or are a polymer of formula (I) or (II) below:

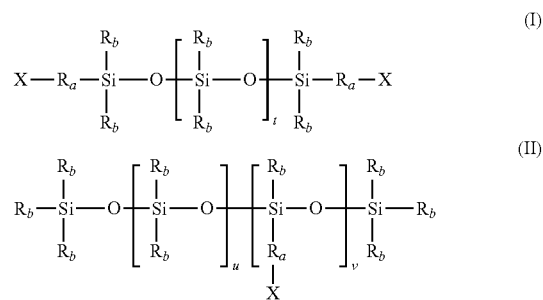

wherein:
$R_a$ denotes a saturated or unsaturated, linear or branched, optionally cyclic, hydrocarbon-based chain comprising from 1 to 100 carbon atoms, optionally interrupted with a heteroatom chosen from N, O, S and P, $R_b$ denotes an alkyl group containing from 1 to 6 carbon atoms or an alkoxy group containing from 1 to 6 carbon atoms, t ranges from 0 to 132, u ranges from 1 to 132, v ranges from 1 to 132, and X represents an acrylate-functionalized group.

3. The composition according to claim 1, wherein the one or more acrylate-functionalized polymer(s) is or are of formula (III) below:

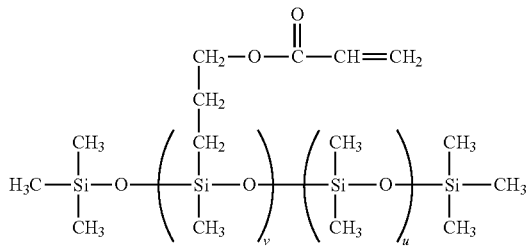

in which u ranges from t to 132, and v ranges from 1 to 132.

4. The composition according to claim 1, wherein the one or more acrylate-functionalized polymer(s) is or are chosen from silicone copolymers of acrylate and of dimethylpolysiloxane.

5. The composition according to claim 1, comprising one or more acrylate-functionalized silicone homopolymers.

6. The composition according to claim 1 wherein the amount of the one or more pigments in the composition ranges from 0.5 to 30% by weight with respect to the weight of the composition.

7. A hair dye comprising the composition according to claim 1.

8. The composition according to claim 1, comprising one or more acrylate-functionalized silicone copolymers.

9. A hair dye comprising the composition according to claim 5.

10. A hair dye comprising the composition according to claim 8.

11. The composition according to claim 5, wherein the amount of the one or more pigments in the composition ranges from 0.5 to 30% by weight with respect to the weight of the composition.

12. The composition according to claim 8, wherein the amount of the one or more pigments in the composition ranges from 0.5 to 30% by weight with respect to the weight of the composition.

13. A composition comprising:
one or more acrylate-functionalized polymers, wherein the one or more acrylate-functionalized polymer(s) is or are chosen from acrylate-functionalized silicone homopolymers and acrylate-functionalized silicone copolymers,
one or more silicones functionalized with one or more mercapto groups, wherein the one or more silicone(s) functionalized with one or more mercapto groups is or are chosen from the compounds of the following formulae:

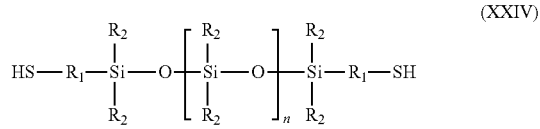

(XXIV)

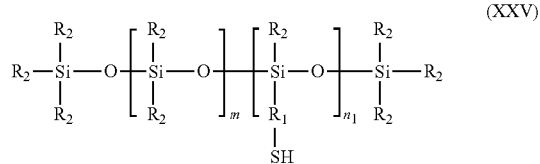

(XXV)

in which
$R_1$ denotes a saturated or unsaturated, linear or branched, optionally cyclic, hydrocarbon-based chain comprising from 1 to 100 carbon atoms, optionally interrupted with a heteroatom chosen from N, O, S and P,
$R_2$ denotes an alkyl group containing from 1 to 6 carbon atoms or an alkoxy group containing from 1 to 6 carbon atoms,
n ranges from 0 to 132,
$n_1$ ranges from 1 to 132, and
m ranges from 1 to 132, and
one or more pigments having solubility in water at 25° C. and 760 mmHg of less than 0.05% by weight.

14. The composition according to claim 13, wherein the one or more acrylate-functionalized polymer(s) is or are a polymer of formula (I) or (II) below:

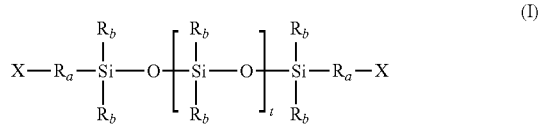

(I)

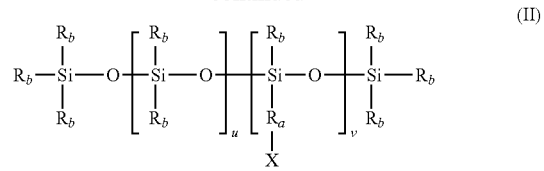

(II)

wherein:
$R_a$ denotes a saturated or unsaturated, linear or branched, optionally cyclic, hydrocarbon-based chain comprising from 1 to 100 carbon atoms, optionally interrupted with a heteroatom chosen from N, O, S and P,
$R_b$ denotes an alkyl group containing from 1 to 6 carbon atoms or an alkoxy group containing from 1 to 6 carbon atoms,
t ranges from 0 to 132,
u ranges from 1 to 132,
v ranges from 1 to 132, and
X represents an acrylate-functionalized group.

15. The composition according to claim 13, wherein the one or more acrylate-functionalized polymer(s) is or are of formula (III) below:

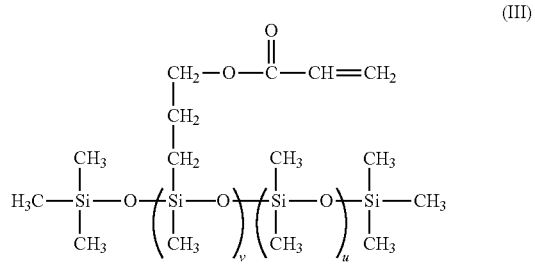

(III)

in which u ranges from 1 to 132, and v ranges from 1 to 132.

16. The composition according to claim 13, wherein the one or more acrylate-functionalized polymer(s) is or are chosen from silicone copolymers of acrylate and of dimethylpolysiloxane.

17. The composition according to claim 13, comprising one or more acrylate-functionalized silicone copolymers.

18. The composition according to claim 13, wherein the amount of the one or more pigments in the composition ranges from 0.5 to 30% by weight with respect to the weight of the composition.

19. A hair dye comprising the composition according to claim 13.

* * * * *